United States Patent [19]
Annis et al.

[11] 4,112,301
[45] Sep. 5, 1978

[54] MOVING PARTICLES SUSPENDED IN A CARRIER FLUID THROUGH A FLOW CHANNEL HAVING AN INPUT END UNDER GAS PRESSURE

[75] Inventors: Martin Annis, Newton; Paul Bjorkholm, Sharon; Carolus M. Cobb, Arlington; Edwin Frederick, Concord; Alan Ramsey, Harvard all of Mass.

[73] Assignee: American Science and Engineering, Inc., Cambridge, Mass.

[21] Appl. No.: 692,322

[22] Filed: Jun. 3, 1976

[51] Int. Cl.² .............................................. G01T 1/20
[52] U.S. Cl. ................................... 250/364; 250/303; 250/432 R; 324/71 CP
[58] Field of Search ................... 250/302, 303, 432 R, 250/432 PD, 364; 424/1; 324/71 CP

[56] References Cited

U.S. PATENT DOCUMENTS

| | | | |
|---|---|---|---|
| 2,985,830 | 5/1961 | Coulter et al. | 324/71 CP |
| 3,742,226 | 6/1973 | Smallbone | 250/432 |
| 3,857,033 | 12/1974 | Cobb | 250/303 |
| 3,912,929 | 10/1975 | Cobb et al. | 250/303 |

Primary Examiner—Harold A. Dixon
Attorney, Agent, or Firm—Pollock, Vande Sande & Priddy

[57] ABSTRACT

Inert gas under pressure forces a suspension of particles in a carrier fluid through a flow channel including tubes of narrow diameter at a pressure high enough to establish laminar flow free from turbulence at a speed determined by a constant displacement rate syringe at the downstream end of the flow channel. At at least two locations along the flow channel measurements are made of particle conditions, such as radioactivity and size, to provide a multiple of particle signals which are correlated to provide a multi-dimensional characterization of the particles, such as the number of cells exceeding a predetermined radioactivity level for each of a number of cell size ranges.

11 Claims, 6 Drawing Figures

THE FOLLOWING HISTOGRAM REPRESENTS THE RADIATION DISTRIBUTION CORRESPONDING TO PARTICLES BETWEEN 5 AND 150μm DIAMETER.

THERE WERE 1034 PARTICLES ANALYZED BELOW.
THIS EQUALS 100% OF TOTAL PARTICLES ANALYZED BETWEEN 5 AND 150μm (TOTAL = 1034); ALSO EQUALS 67% OF TOTAL PARTICLES DETECTED BETWEEN 5 AND 150μm (TOTAL = 1541).

TOTAL SCINTILLATION COUNTS BELOW = 14142 = 100% OF TOTAL FOR ALL PARTICLES ANALYZED (TOTAL = 14142).

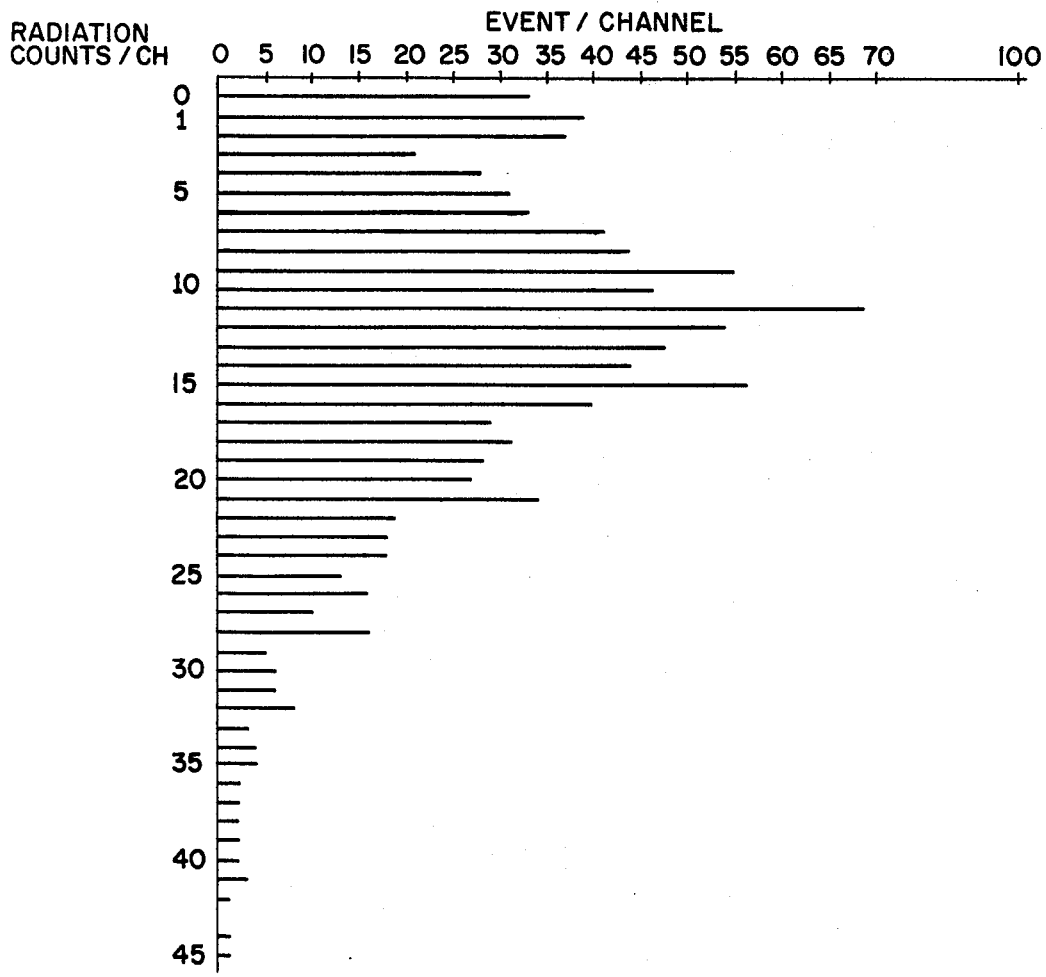

FIG. 4

MOVING PARTICLES SUSPENDED IN A CARRIER FLUID THROUGH A FLOW CHANNEL HAVING AN INPUT END UNDER GAS PRESSURE

BACKGROUND OF THE INVENTION

The present invention relates in general to particle moving and more particularly concerns novel techniques and apparatus for establishing laminar flow in tubes of small diameter so that small particles, such as cells, may be examined one-by-one and the passage of each by a counting point related to the passage at a radiation or other characteristic measuring point. A system according to the invention is especially suitable for automatically measuring radiation from each of a sequence of cells for detecting malignant cells generally in accordance with the techniques disclosed in U.S. Pat. Nos. 3,857,033 and 3,780,291.

The latter patent describes a system in which cells suspended in a fluid flow past one of a particle detector and radiation detector and then the other. While that system produced useful results, there were a number of inaccuracies. The source of these inaccuracies was not easily discovered. It was discovered that one source of error is turbulence developing in the flow channel making it difficult to associate the detection of a cell with the radiation from the detected cell.

Accordingly, it is an important object of the invention to provide improved methods and means for measuring characteristics of each of a plurality of particles.

It is another object of the invention to achieve the preceding object while overcoming one or more of the problems encountered in the prior art.

It is another object of the invention to achieve one or more of the preceding objects while inducing particle dispersion.

It is still another object of the invention to achieve one or more of the preceding objects with a stable flow rate while avoiding particle blockage.

It is yet another object of the invention to achieve one or more of the preceding objects while reducing contamination.

It is a further object of the invention to achieve one or more of the preceding objects while automatically detecting a sample containing malignant cells.

SUMMARY OF THE INVENTION

According to the invention, a suspension of particles maintained in a carrier fluid is forced through a flow channel while the speed of flow of the suspension through the flow channel is controlled by regulating the rate of increase in the volume of a sink at the channel output. The suspension is preferably forced through the flow channel at a pressure that would produce a higher flow rate in the absence of this regulation. At a number of spaced locations along the flow channel, at least two time-spaced sensings of a particle occur to provide at least two time-spaced signals associated with a particle. Preferably, the suspension flows through the flow channel in a particle-by-particle flow series with one of the associated signals being representative of the particle passing a reference point and at least another representative of a characteristic of that particle identifiable by associating the known substantially constant flow velocity with the known space between sensing locations. Preferably the suspension is forced through the flow channel by immersing the entrance to the flow channel in the suspension, and sealing both the suspension and the channel entrance in a pressure chamber which is then pressurized to drive the suspension into the flow channel. Another feature of the invention is a stirrer in the chamber that receives stirring torque through magnetic coupling means from a motor or other driving source outside the pressure chamber.

Numerous other features, objects, and advantages of the invention will become apparent from the following specification when read in conjunction with the accompanying drawing in which:

BRIEF DESCRIPTION OF THE DRAWING

FIG. 4 is a typical histogram plotted by a computer output line printer.

DETAILED DESCRIPTION OF PREFERRED EMBODIMENTS

Figure 1:
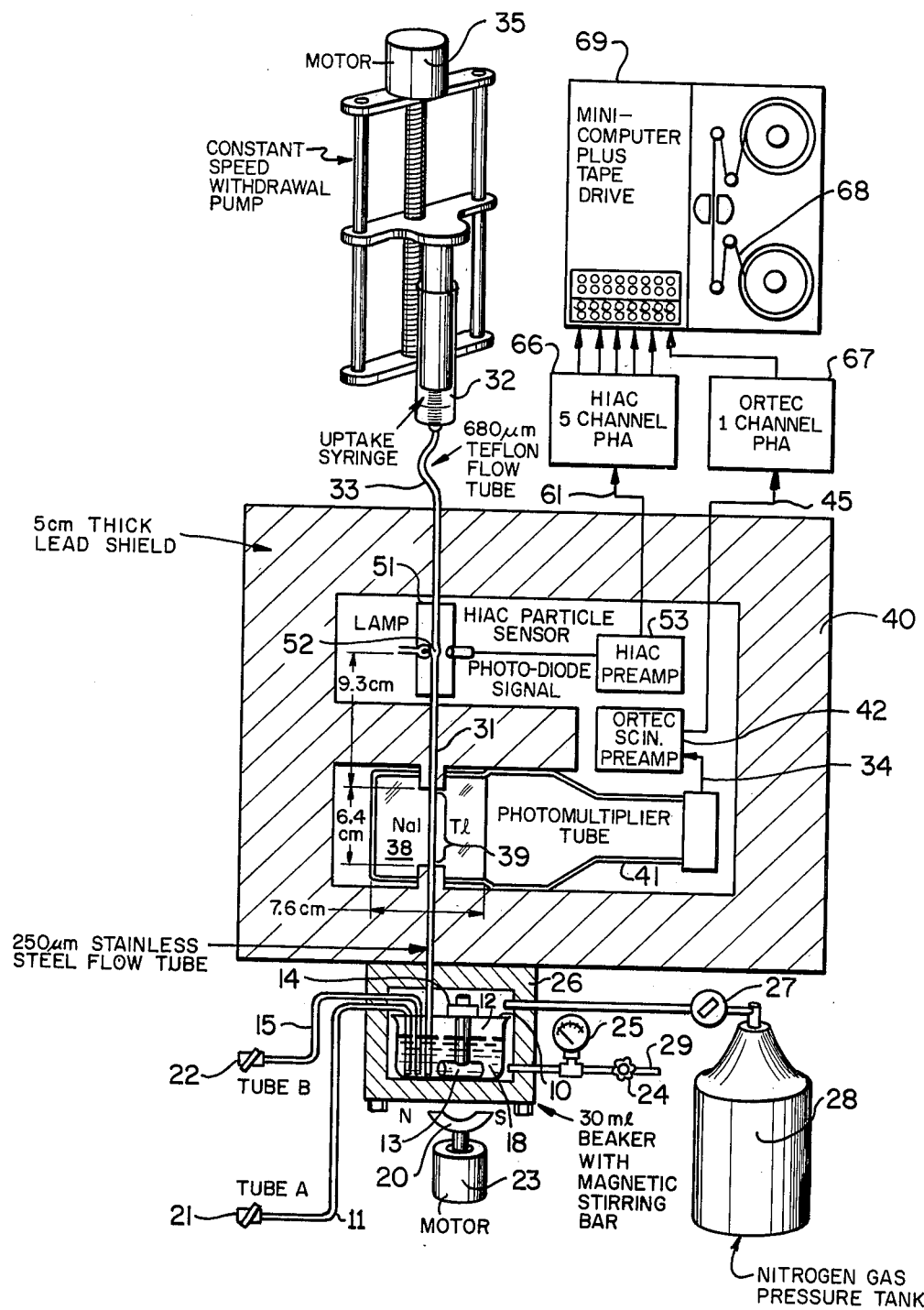
FIG. 1 is a combined block-pictorial diagram of an exemplary embodiment of the invention for measuring radioactivity of each of a number of particles.

With reference now to the drawing and more particularly FIG. 1 thereof, there is shown a combined block-pictorial diagram of a system according to the invention for detecting radioactivity of each of a number of particles. Minicomputer 69 provides histograms showing number of cells as a function of cell radioactivity for each of a number of size classifications in response to signals developed as cells traverse flow channel 31 from pressure chamber 26 to uptake syringe 32 and pass scintillator crystal 38 and Hiac particle sensor 51.

Ethyl alcohol and a sample of radioactive cells enter beaker 12 in pressure chamber 26 through A tube 11 and B tube 15, respectively. Motor 23 is magnetically coupled to stir bar 13 for stirring the essentially uncontaminated cell suspension 18. The stirring continues to maintain the cells in suspension while closing valves 21, 22 and 24 to seal pressure chamber 26 and then opening valve 27 to admit gas from tank 28 pressurizing chamber 26 to force suspension 18 up flow channel tubes 31 and 33 toward uptake syringe 32. Motor 35 drives uptake syringe 32 at a regulated speed to withdraw suspension from flow channel 31 at a regulated rate and thus control the speed of flow through flow channel tubes 31 and 33. Uptake syringe 32 thus functions as a sink connected to the output of the flow channel for receiving the suspension therefrom at a rate determined by the rate of increase in its volume to establish an increased pressure at the output end that determines the average speed of the suspension through the flow channel.

NaI(Tl) scintillator crystal 38 at location 39 along flow channel tube 31 responds to the radioactivity of each particle flowing past location 39 to produce scintillations sensed by photomultiplier tube 41 to provide a particle radioactivity signal over output line 34 for amplification by preamplifier 42. A Hiac particle sensor 51 at location 52 connected to the end of flow channel tube 31 responds to cells flowing past location 52 to provide a particle signal representative of cell size over output line 61 of preamplifier 53. Pulse height analyzers 66 and 67 respond to cell size and radioactivity signals on lines 61 and 45, respectively, to provide output signals that are processed by minicomputer 69 and recorded on digital magnetic tape 68 to produce histograms of cells according to radioactivity and size. A lead radiation shielding chamber 40 houses the indicated components of the radiation and particle detecting systems. In an actual embodiment of the invention data were analyzed and histograms printed by an off-line computer (IBM System/370) as outlined below.

Beaker 12 is also emptied through A and B tubes 11 and 15, respectively, typically comprising 760 μm I.D. stainless steel tubing inside pressure chamber 26 and respectively 680 μm I.D. and 300 μm I.D. Teflon tubing outside pressure chamber 26. A tube 11 and B tube 15 terminate respectively in contact with and just above (typically 3 mm.) the bottom of beaker 12 to facilitate emptying and cleaning.

The stirring system comprises Teflon coated magnetic stir bar 13 typically 1.0 cm. long by 0.9 cm. in diameter driven by a coaxial magnetic yoke 20 beneath beaker 12 carried by motor 23. To minimize contamination by dirt particles, a sealed ball bearing cage and dirt trap 14 on aluminum beaker cover 10 rotatably supports the stainless steel stem of stir bar 13. The dirt trap catches any particles emitted by the rotating connection. The bottom of stir bar 13 does not rub on the bottom of beaker 12. To reduce the formation of any pattern in particle density, the spin axis of stir bar 13 is preferably one third the beaker diameter D from the edge, D typically being 4 cm. A suitable spin speed to maintain a uniform particle distribution was found to be 300 rpm.

Flow channel tube 31 preferably comprises a unitary straight stainless steel flow tube free from turbulence-causing joints or other obstructions with its lower end one millimeter above the bottom of beaker 12 passing through an aluminum lined hole typically 6.8 mm. in diameter in the center of scintillator crystal 38 and its upper end connected to the input of the Hiac particle cell having a 150 × 500 μm rectangular fluid passage. Teflon flow tube 33 completes the flow channel between Hiac particle sensor 51 and uptake syringe 32. A smooth transition is preferably made between the circular cross section flow tubes 31 and 33 and the rectangular fluid passage of particle detector 51 with the cross sectional area of each substantially the same. All connections preferably avoid voids, constrictions or abrupt changes in flow channel diameter to avoid turbulence. Particle sensing location 52 and radiation sensing location 39 are preferably as close together as practical.

At the output end of the flow channel uptake syringe 32 is easily removable for emptying and cleaning. At the input end nitrogen pressure tank 28 supplies and a standard reduction valve 27 regulates gas flow to pressurize chamber 26. Gauge 25 indicates the gas pressure, which may be released through outlet line 29 by opening valve 24.

In the exemplary embodiment of the invention shown in the drawing, a conventional photomultiplier-preamp-pulse height analyzer chain 41, 42, 67 amplifies and analyzes the scintillations from crystal 38. Preferably, pulse height analyzer 67 is adjusted to accept only pulses characteristic of the gamma radiation from the cells being examined. In one application, cells scraped from a human uterine cervix and processed with a Gallium salt carry a $^{67}$Ga radioactive tracer as an indicator of malignancy. In this application, the pulse height analyzer window is narrowly adjusted to accept 93 keV photons, although the signal-to-noise ratio could be slightly increased by adding a second pulse height analyzer to include the 185 keV photons, and by adding an OR gate for combining the two analyzer outputs. The Hiac particle detector 51, preamp 53 and five-channel pulse height analyzer 66 shown in the exemplary embodiment are all commercially available units. This apparatus typically detects cells in the range 5 to 150 μm and separates the detected signals into five size subranges within the 5 to 150 μm range. Since most specific elements of the system are known to those skilled in the art who can practice the invention from an examination of the drawing and the accompanying description, further specific details are omitted so as to avoid obscuring the invention.

A feature of the invention is that the forced flow-controlled withdrawal system provides stable, nonturbulent, laminar flow that prevents particle blockage.

The pressure required by the $N_2$ gas to force a laminar flow of liquid of viscosity $\eta$ through a cylindrical tube at an average speed $<v>$ is given approximately by the Hagen-Poiseuille law $$P = 32(\eta l/D^2) <v> \tag{1}$$

The dimensions of the flow tube 31 are D = 250 μm I.D. and $l$ = 27.5 cm. long. The viscosity of the ethyl alcohol at 20° C. is 1.2 cpoise. An efficient average flow speed is typically $<v>$ = 7.0 cm/s. This requires a value of P = 2 psig. Since the liquid must also be forced through the particle detector 51, through ≈ 10 cm. of 680 μm Teflon tubing 33, and into an uptake syringe, the actual pressure needed is ≈ 4 psig.

However, for a constant pressure, P, the average flow speed $<v>$ will change each time a particle sticks to or leaves a flow channel wall. By setting P higher, typically about 30 psig and regulating the withdrawal velocity in the uptake syringe 32 where V represents the fluid volume there and $\dot{V}$ its time derivative, $\dot{V}$ determines the average flow velocity $<v>$, typically 7.0 cm/s. $\dot{V}$ is preferably constant and established by connecting withdrawal syringe 32 to synchronous motor 35 comprising a constant speed withdrawal pump that withdraws the syringe plunger at constant velocity. As long as the pressure P is sufficient to overcome any minor constriction in the tube, such as caused by particle sticking, the average flow is given by $$<v> = \dot{V}/A, \tag{2}$$

where A is the cross sectional area of the flow channel. The back pressure provided by the excess pressure against uptake syringe 32 also prevents excess decompression that might produce bubbles detected by particle detector 51. Other features of the invention discussed above help prevent turbulence and achieve laminar flow in the flow path embracing radiation detector 38 and location 52. For a flow tube of I.D. 250 μm, alcohol of viscosity 1.2 cpoise, and average velocity $<v>$ of 7.0 cm/s, fluid flow becomes laminar after a distance of only 375 μm into the flow tube, which is well before entering scintillator crystal 38 where the velocity profile is parabolic and given by $$v(r) = v_{max}[1 - (r^2/R^2)] \tag{3}$$

where $r$ is the radial distance from the cylindrical axis, R is the radius of the flow tube and $v_{max}$ is the velocity on axis. It has been discovered that particles tend to concentrate within the central region of the flow tube.

For neutrally buoyant easily deformable particles in a Poiseuille flow as given in Eq. (3), the steady state radial position is on the axis. The amplitude of the radial restoring force depends in a complicated way upon many factors such as radial distance, particle and tube size, center velocity and viscosity of the fluid, buoyancy, deformability and other factors. If neutrally buoyant rigid particles are used in the system, the radial restoring force will be much smaller, with equilibrium not at $r = 0$, but at $r = R/2$.

The invention may take many forms. For example, a color sensitive instrument that detects the uptake of the dye in a cell may be used in combination with a particle sizer, or three measuring instruments may be placed at three measurement locations along the flow channel and their outputs correlated.

In any form, the invention has numerous uses. For example, the form of the instrument that measures particle radioactivity and size is applicable in such fields as cytology (e.g., cancer detection and research), ecology (e.g., pollutant effects on microorganisms), hydrodynamics (e.g., particle tracers), mechanical engineering (e.g., machine wear), and many others. Although a specific use of the invention is for measuring cell characteristics, the invention is suitable for use in any particle measuring or detecting system.

To correlate each radiation burst detected by scintillation crystal 38 with the proper particle passing location 52, the transit time $t_t$ between the center of scintillator crystal 38 and location 52 must be known. It is convenient to assume that there is homogeneous distribution of $N_o$ particles on a surface plane at $z = z_o$ for all values of $0 \leq r \leq R$, and that each particle maintains a fixed radial distance r. At $z = z_o$ the number of particles between r and $r + dr$ is given by $$dN(r) = (N_o/A)\, dA(r) = (N_o/A)\, 2\pi r dr. \quad (4)$$

It therefore follows from Eqs. (3) and (4) that $$(dN/dt) = (dN/dA)(dA/dr)(dr/dv)(dv/dt)$$

where $t$ is the transit time. Therefore the distribution at $z = z_o + l$ is $$\frac{dN}{dt} = \left(\frac{N_o}{A}\right)(2\pi r)\left(\frac{-R^2}{2v_{max}r}\right)\left(\frac{-l}{t^2}\right)$$

$$= \frac{N_o l}{v_{max} t^2} = \frac{N_o t_{min}}{t^2} \text{ for } t > t_{min};$$

where $t_{min} = l/v_{max}$.

Figure 2:
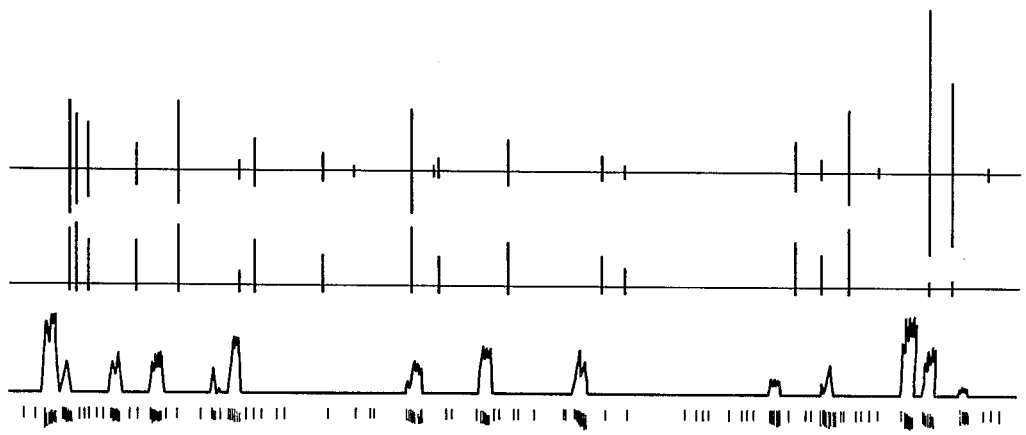
FIG. 2 is an oscillograph recording of the data from the system of FIG. 1.

Referring to FIG. 2, there is shown a graphical representation of a chart recording of data actually measured in accordance with a system according to the invention. The lower two traces represent the response from the logic output of scintillator pulse height analyzer 67. Specifically, the lowest trace is the output of pulse height analyzer 67; these pulses are applied to a typical count-rate circuit not shown in FIG. 1, the output of which is shown in the trace immediately above the lowest trace. The upper two traces represent the particle sizes provided by Hiac pulse height analyzer 66. Specifically, the highest trace represents the signal on line 61; each of the five channel responses from pulse-height analyzer 66 is represented by a unique pulse height in the trace immediately below the highest trace. The width of each isolated strong burst of radiation approximately represents the transit time $t_{NaI}$ of the order of 0.6 seconds of a radioactive particle through scintillator crystal 38. In the specific embodiment the various dimensions were such that the particle should be detected upon passing location 52 at a time centered on the order of $2t_{NaI}$ after it passes the center of scintillator crystal 38.

Traces move left to right with increasing time. The bottom trace displays standardized NaI scintillation crystal 38 pulses from individual 93 keV photons. These pulses are applied to a typical count-rate circuit (0.06 s time constant) and are displayed immediately above. Output of the Hiac sensor preamp 53 is shown in the very top trace; the amplitudes (neglecting undershoot) should be proportional to the particles' aspect area. These pulses are applied to 5-channel PHA 66; each channel response is represented by a unique pulse height in the trace immediately below. The channel boundaries are at 5, 7, 10, 15, 25 and 150 μm diameter.

The first radioactive burst at the left has a double peak and becomes saturated on the second peak. Saturation of the halvanometer driver occurs for a uniformly spaced count rate greater than 100 ct/s. This double-peaked burst indicates that the first two particles are too close to each other to be analyzed. Radiation from the third particle is just totally resolvable. Radiation from the fourth particle is clearly isolated. The next four particles are each recorded in all but the largest Hiac pulse height analyzer size channel. The last small burst of radiation at the right is produced by two nearly unresolvable particles less than 5 μm in diameter without any responses from the Hiac pulse height analyzer 66.

A preferred and more versatile method of data analysis comprises minicomputer 69, such as a Data General Nova which may be used to sort the digital data for recording upon a digital 9-track magnetic tape. Six lines of digital pulse height analyzer data from analyzers 66 and 67 are recorded as a sixteen bit digital number every ten milliseconds. This arrangement preserves raw data so that the analysis may be performed many tmes; each run may vary in the method of analysis and the effects resulting from a change in any analytical parameter may be tested.

Figure 3A:
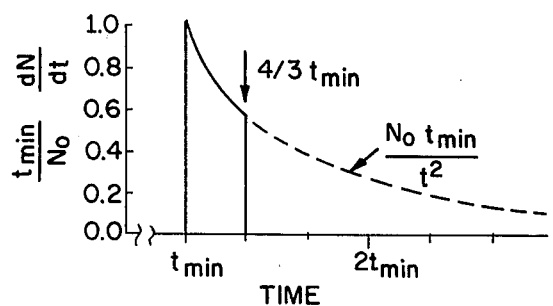
FIGS. 3a–3C show the relationship between predicted and observed particle transit time distributions.
Figure 3B:
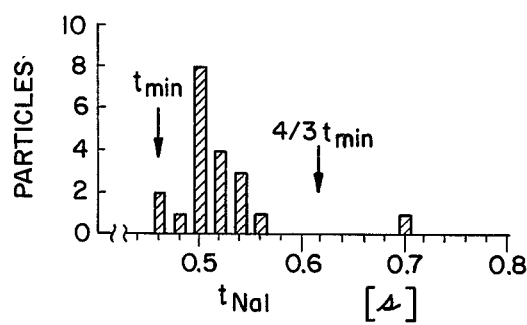
Figure 3C:
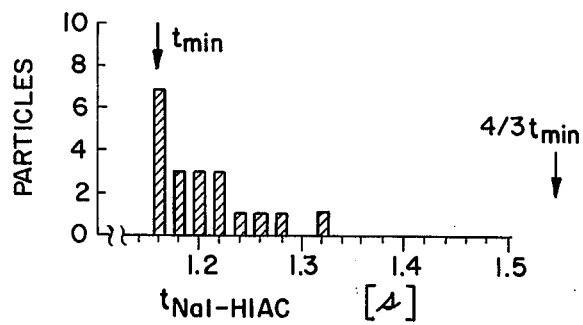

Referring to FIG. 3A, there is shown a graphical representation of $(t_{min}/N_o)(dN/dt)$ as a function of time where $dN(r)$ in equation (4) is restricted to $r \leq R/2$. This plot shows the expected distribution, for laminar flow, of nonmigrating particles uniformly spread within the central quarter area of the flow tube. The transit time $4/3 t_{min}$ corresponds to motion at $r = R/2$. Referring to FIGS. 3B and 3C, there are shown histograms representing observed values of $t_{NaI}$ and $t_t$, respectively, for the same twenty prominent events (> 200ct/s recorded at 7.0 cm/s average velocity) from high speed (2.54cm/s), time-marked oscillograph recordings. Although there is some fluctuation in radial position of a particle as a function of its position along the flow path and 23% of the flow path $l_f$ from the center of scintillation crystal 38 to location 52 which was 12.5 cm was not cylindrical because of the circular to rectangular transition from the junction at the top end of flow tube 31 to the light beam at location 52, the similarity between the predicted distribution of FIG. 3A and the measured distribution of FIG. 3C indicates that the transition was good and the slight fluctuations in radial position do not appreciably affect the value of the results.

The data signals derived from a system according to the invention may be analyzed in a number of ways. One method involves using the Nova minicomputer 69. Data for each particle in a sample may be analyzed and assembled into a histogram in accordance with techniques well-known in the art. Evolution of the histogram in real time may be displayed on a CRT (not shown). A second method may use a multi-channel analyzer whereby histogram data for all five particle diameter ranges may be displayed simultaneously by some analyzers as an isometric 3-D plot on a CRT.

Alternatively, the data may be analyzed off-line, such as with an IBM System/370 computer. Data recorded on the six channels as described above may be used as the input for the off-line computer. Using computer program techniques known in the art, the tape buffer may be first scanned for a Hiac particle response. When found, a further scan for a second particle may be made over a tape buffer length equal to $t_{dead}$ (dead time of data). If not unique, $t_{dead}$ of data after the second particle may be skipped, and the search recommenced for an isolated particle. When found, i.e., when no other particle within $\pm t_{dead}$ exists, all of the radiation counts are tallied over the time segment $$t_{Hiac} - t_{tr} - \tfrac{1}{2} t_w$$

$$t_{Hiac} - t_{tr} + \tfrac{1}{2} t_w$$

where $t_{Hiac}$ is the Hiac responding time; $t_{tr}$ is the transit time between the center of the crystal 38 and particle detector location 52 and $t_w$ is a temporal window width preset for tallying radiation counts chosen to be large enough to include most values of $t_{NaI}$, the transit time through crystal 38, plus half of most of jitter in $t_{tr}$. The dead time is preferably set so that $t_{dead}$ is greater than $t_w$ with a large inequality allowing minimal cross talk at reduced efficiency. For a fixed value of $t_{dead}$, the optimum density of flow particles for a maximum number analyzed in a given period is when $1/e$ of the particles are accepted because the maximum count rate occurs when $1/e$ of the true count rate is measured. Upon completion of analysis of the data recorded on a tape before a given run, histograms for the various particle size ranges may be automatically plotted by the computer output line printer. Referring to FIG. 4, there is shown an example of such a histogram.

The distribution represents the number of isolated ($t_{dead} = 0.8$ s) particles (range 5 - 150 μm diam.) as a function of radiation recorded per window width $t_{window} = 0.8$ s ($t_{NaI} \approx 0.6$ s), where the window center was set at $t_{tr} = 1.25$ s prior to the Hiac response.

The average background radiation represented in the histogram of FIG. 4 is only 0.4 ct/$t_w$ = 0.5 ct/s determined from counts remote from the detected particles as recorded on an oscillograph. The radiation recorded by a scaler before and after this particular run was also 0.5 ct/s caused by 0.3 ct/s of photomultiplier tube dark current and 0.2 ct/s of $^{67}$Ga contamination on the wall of the flow tube deposited from the numerous prior runs. The $^{67}$Ga in the suspension alcohol contributes only 0.01 ct/s, the liquid volume within the scintillator crystal 38 being 3.1 μl. The $^{67}$Ga uptake by the wall of the flow tube 31 within the scintilaor crystal 38 was typically 0.1 ct/s per 10 hours of continuous running.

After each run it is preferble to clean the system with 120 ml of 0.2 μm filtered alcohol. Since sample beaker 12 contains most of the contaminates (particle noise), cleaning is facilitated by twice injecting, then ejecting, 40 ml of alcohol through A tube 11. After such cleaning, only about 1 particle/ml was detected for 0.2 μm filtered alcohol with stirring on.

Although the specific test results were in connection with using $^{67}$Ga, any γ-emitter may be used whose emission energy is greater than 30 keV provided that the carrier element or molecule possesses such characteristics (usually chemical) that its uptake is a function of the microparticle property to be studied for use. The thinnest stainless steel wall tubing commercially available at the time the invention was made absorbs γ-rays so that detecting emitters with less energy is difficult. If lower Z material is used, lower emission energy may be acceptable. For use with the 0.5 mm thick aluminum hole liner in the scintillator crystal, the emission energy could be as low as 20 keV.

While any γ-emitter can be utilized whose emission energy is > 30 keV, the efficiency of a 7.6 × 7.6 cm NaI(Tl) scintillator crystal 38 drops to a minimum of 25% at 5 MeV. Furthermore, the shielding ability of lead is a minimum at 3.2 MeV so that the $t_{NaI}$ at 3.2 MeV would be three times $t_{NaI}$ at 93 keV. Consequently, the preset dead time $t_{dead}$ is preferably tripled to avoid including counts from an adjacent particle, if 3.2 MeV γ-radiation is utilized.

Another consideration is the value of the decay costant τ of the radioactive tracer. If the measured activity is sufficient for any value of τ, then the ideal choice is the largest value of τ possible. Otherwise, if only $M = (N^* + N)/n$ molecules can be induced into each particle, where $N^*$ and $N$ are the number of tracer and nontracer nuclei respectively, and $n$ is the number of atoms per molecule, then the optimum value of τ will depend upon T, the elapsed time between particle inoculation and the subsequent passage through the scintillator crystal 38. The measured activity is then $$I(T) = (N^*/\tau) \epsilon^{-T/\tau}.$$

Maximizing $I(T)$ with respect to τ yields $\tau = T$. That is to say, the preferred decay constant τ is equal to the elapse period T; of course T should be kept to a practical minimum.

The foregoing description is sufficient to enable anyone skilled in the art to practice the invention. For further specific guidance, the constant speed withdrawal pump is available from Harvard Apparatus Company, Inc. of Millis, Mass. Filter holders and Teflon filters suitable for use in and with the system are available from Millipore Corporation. The particle detector is available from High Accuracy Products Corporation of Claremont, Calif., including the sensor cell, the sensor preamp and the 5-channel pulse height analyzer. The sensor cell is a modified D-5-150 in which a light beam passes normal to a 150 × 500 μm rectangular fluid path and through a 150 × 150 μm window to the photodiode. The width of the fluid passage matches the window width so that all particles are fully measured. The depth of the fluid passage is chosen so that its cross sectional area approximately matches that of the stainless steel flow tube 31. A smooth transition is made from the circular to rectangular cross section. All particles are sized according to their cross sectional area as viewed from the window. A particle is detected by the reduction of the light beam intensity due to any combination of absorption, reflection and refraction provided that the index of refraction of the particles is different from that of the carrier fluid.

A suitable oscillograph is available from Consolidated Electrodynamics Corporation of Pasedena, Calif.

Both stainless steel and Teflon tubing with small inner diameter are available from the Hamilton Company of Reno, Nev.

A specific embodiment of the invention measures the in vitro uptake of $^{67}$Ga in exfoliated epithelial cells from the human uterine cervix.

It was discovered that nearly all materials become highly radioactive when submerged in concentrated $^{67}$Ga Cl$_3$. This discovered property of $^{67}$Ga Cl$_3$ was used to measure dirt contamination due to the various containers and filters while handling biological cells.

For a detailed description of the use of a gallium compound, reference is made to U.S. Pat. No. 3,857,033 A brief summary of the procedure for affiliating cells with $^{67}$Ga follows.

The samples analyzed are scrapings taken from the human uterine cervix which would normally be used for a Papanicolaou test. Each sample is suspended in 1 ml of clear fixing solution consisting of $\approx 86\%$ ethyl alcohol. A cellular population of typically 50,000 cells is first filtered through a 55 $\mu$m steel mesh; the epithelial cells of interest generally range from 10 to 40 $\mu$m diameter in the ethanol. The 1 ml sample is then added to a 1.5 ml solution of $^{67}$GaCl$_3$ (assayed at $\approx 1$ mCi) and allowed to soak for at least 1 hour; equilibrium for the radioactive uptake by these cells occurs after $\approx 20$ minutes.

Next the suspended cells are transferred from the radioactive liquid to pure ethyl alcohol. This is accomplished by first filtering the liquid through a 10 $\mu$m polycarbonate filter, and then replacing this waste alcohol with an equal volume of pure alcohol. This two step process is then repeated at least 6 times. The resulting concentrated sample of cells has a typical activity of $\approx 1$ nCi/cell suspended in alcohol whose activity is $\approx 1$ nCi/ml ready for analysis by the system of FIG. 1.

There has been described novel laminar flow methods and apparatus that afford rapid and precise automated measurements of multi-dimensional characterization of particles along with many features. It is evident that those skilled in the art may now make numerous uses and modifications of and departures from the specific embodiments described herein without departing from the inventive concept. Consequently, the invention is to be construed as embracing each and every novel feature and novel combination of features present in or possessed by the method and apparatus herein disclosed.

What is claimed is:

1. A method of moving particles suspended in a carrier fluid through a flow channel which method includes the steps of,
   introducing the suspension of the particles in the carrier fluid into said flow channel,
   applying gas pressure at the input end of said flow channel,
   establishing a proper variable pressure at said output end to establish substantially constant average velocity of said suspension through said flow channel,
   applying mechanical pressure at the output end of said flow channel so that the rate of flow of said suspension through said flow channel is determined by the mechanical pressure at said output end by withdrawing a plunger connected to the output end of said flow channel at constant velocity,
   and applying gas under pressure into a sealed chamber embracing a liquid container,
   the said liquid container embracing the input end of said flow channel.

2. A method of moving particles in accordance with claim 1 and further including the step of establishing laminar flow in a predetermined continuous portion of said flow channel.

3. A method of moving particles in accordance with claim 2 and further including the steps of detecting a characteristic of each particle at predetermined spaced points along said predetermined portion.

4. A method of moving particles in accordance with claim 1 and further including the steps of detecting the occurrence of a particle at one of said spaced points and detecting a radiation characteristic of said particle at another of said spaced points.

5. A method of moving particles in accordance with claim 4 and further including the steps of providing signals representative of the detection of a particle and its radiation characteristic at different times,
   storing at least one of the latter signals,
   and combining signals representative of detection of a particle and its radiation characteristic to provide a representation of the occurrence of a particle and its radiation characteristic.

6. A method of moving particles in accordance with claim 1 and further including the steps of introducing said suspension into said liquid container to a level covering the input end of said flow channel,
   and stirring said suspension.

7. A method of moving particles in accordance with claim 6 and further including the step of rotating a stirring rod about an axis of rotation asymmetrically located in said liquid container.

8. Particle moving apparatus for practicing the method of claim 1 comprising,
   said flow channel,
   sources of said gas pressure and said mechanical pressure,
   means for coupling the gas pressure source to the input end of said flow channel,
   and means for coupling the mechanical pressure source to the output end of said flow channel while coupling the mechanical pressure source to the output end of said flow channel so that the rate of flow of said suspension through said flow channel is determined by the mechanical pressure at said output end,
   wherein said mechanical pressure source comprises a constant speed withdrawal pump and said gas pressure source comprises a source of gas under pressure,
   and the means for coupling said gas pressure source to said input end comprises a sealed chamber with said liquid container for carrying said suspension prior to entering said input end having an inlet for receiving said gas under pressure.

9. Particle moving apparatus in accordance with claim 8 and further comprising,
   stirring means inside said liquid container for stirring said suspension.

10. Particle moving apparatus in accordance with claim 9 wherein said stirring means is rotatable about an axis asymmetrically located in said liquid container.

11. Particle moving apparatus in accordance with claim 10 wherein said stirring means comprises an inverted T-shaped element having a cap of magnetic material closely adjacent to but spaced from an inside surface of said sealed chamber rotatably supported from the stem portion, a magnetic element outside said sealed chamber closely adjacent to the outside of said inside surface for magnetically transferring a torque to said cap, and means for moving said magnetic element to cause movement of said stirring means.

* * * * *